United States Patent
Goto et al.

(10) Patent No.: US 10,125,081 B2
(45) Date of Patent: Nov. 13, 2018

(54) METHOD FOR PRODUCING CARBOXYLIC ACID ANHYDRIDE AND METHOD FOR PRODUCING CARBOXYLIC ACID ESTER

(71) Applicant: Mitsubishi Chemical Corporation, Tokyo (JP)

(72) Inventors: Akihiro Goto, Otake (JP); Yoshihiro Kamon, Toyohashi (JP)

(73) Assignee: Mitsubishi Chemical Corporation, Tokyo (JP)

( * ) Notice: Subject to any disclaimer, the term of this patent is extended or adjusted under 35 U.S.C. 154(b) by 0 days.

(21) Appl. No.: 15/315,775

(22) PCT Filed: Jun. 4, 2015

(86) PCT No.: PCT/JP2015/066181
§ 371 (c)(1),
(2) Date: Dec. 2, 2016

(87) PCT Pub. No.: WO2015/186787
PCT Pub. Date: Dec. 10, 2015

(65) Prior Publication Data
US 2017/0088502 A1 Mar. 30, 2017

(30) Foreign Application Priority Data

Jun. 4, 2014 (JP) .................. 2014-115386

(51) Int. Cl.
| | |
|---|---|
| *C07C 51/54* | (2006.01) |
| *C07C 51/56* | (2006.01) |
| *C07C 53/00* | (2006.01) |
| *C07C 57/02* | (2006.01) |
| *C07C 67/08* | (2006.01) |
| *C07C 67/28* | (2006.01) |
| *C07B 61/00* | (2006.01) |

(52) U.S. Cl.
CPC .............. *C07C 67/28* (2013.01); *C07C 51/54* (2013.01); *C07C 51/56* (2013.01); *C07C 53/00* (2013.01); *C07C 57/02* (2013.01); *C07C 67/08* (2013.01); *C07B 61/00* (2013.01); *C07C 2601/14* (2017.05)

(58) Field of Classification Search
CPC .......... C07C 67/28; C07C 51/54; C07C 51/56
See application file for complete search history.

(56) References Cited

U.S. PATENT DOCUMENTS 4,792,620 A * 12/1988 Paulik .................. B01J 31/0231
560/232
8,859,804 B2 * 10/2014 Ansai ...................... C07C 67/08
560/205

FOREIGN PATENT DOCUMENTS

JP 2000-191590 A 7/2000

OTHER PUBLICATIONS

Wikipedia, Wikipedia , Tilde, recovered from https://en.wikipedia.org/wiki/Tilde on Mar. 23, 2017, pp. 1-19. (Year: 2017).*
Norskov et al (Nature Chemistry, Towards the Computational Design of Solid Catalysts, 2009, 1, pp. 37-46. (Year: 2009).*
Bartoli et al, Synthesis, Reaction of Dicarbonates with Carboxylic Acids Catalyzed by Weak Lewis Acids: General Method for the Synthesis of Anhydrides and Esters, 2007, 22, pp. 3489-3496. (Year: 2007).*
Giuseppe Bartoli, et al., "Reaction of Dicarbonates with Carboxylic Acids Catalyzed by Weak Lewis Acids: General Method for the Synthesis of Anhydrides and Esters," Synthesis, No. 22, Sep. 25, 2007, (9 pages).
L. Goossen, et al., "Lewis Acids as Highly Efficient Catalysts for the Decarboxylative Esterification of Carboxylic Acids with Dialkyl Dicarbonates," Adv. Synth. Catal., 2003, vol. 345, pp. 943-947.
Hallena Rogers, et al., "A Novel and Facile One-Pot Method for the Synthesis of N-Substituted Sulfamates," Synthesis, No. 14, Jul. 2, 2008, (7 pages).
V. F . Pozdnev, "Synthesis of N-furylacryloyl derivatives of amino acids and peptides-chromogenic substrates of proteolytic enzymes-using furylacrylic anhydride," Zhurnal Obshchei Khimii, vol. 56, No. 3, 1986, (7 pages).
Letizia Sambri, et al., "Recent Developments on the Synthesis and Cleavage of tert-Butyl Ethers and Esters for Synthetic Purposes and Fuel Additive Uses," Current Organic Synthesis, 2012, vol. 9, No. 1, pp. 137-148.
International Search Report dated Jul. 28, 2015 in PCT/JP2015/066181 filed Jun. 4, 2015.

* cited by examiner

*Primary Examiner* — Paul A Zucker
(74) *Attorney, Agent, or Firm* — Oblon, McClelland, Maier & Neustadt, L.L.P.

(57) ABSTRACT

Provided is a production method whereby corresponding carboxylic acid anhydrides and carboxylic acid esters can be obtained at high yield from various carboxylic acids even without a solvent and near room temperature. A method for producing a carboxylic acid anhydride represented by formula (II), the method comprising reacting a compound represented by formula (I) and a carboxylic acid in the presence of a Group II metal compound having an ionic ligand containing an oxygen atom. A method for producing a carboxylic acid ester, the method comprising reacting a carboxylic acid anhydride produced by the aforementioned method and an alcohol. In formula (I), $R^1$ represents a $C_{1-20}$ hydrocarbon group. In formula (II), $R^2$ represents a $C_{1-20}$ hydrocarbon group.

19 Claims, No Drawings

METHOD FOR PRODUCING CARBOXYLIC ACID ANHYDRIDE AND METHOD FOR PRODUCING CARBOXYLIC ACID ESTER

TECHNICAL FIELD

The present invention relates to a method for producing a carboxylic acid anhydride and to a method for producing a carboxylic acid ester.

BACKGROUND ART

Carboxylic acid anhydrides are used as raw material for producing esters and amides. A method known to produce carboxylic acid anhydrides is to react di-t-butyl dicarbonate and carboxylic acid. Non-Patent Literature 1 describes a method for producing a carboxylic acid anhydride by reacting di-t-butyl dicarbonate and carboxylic acid in tetrahydrofuran in the presence of magnesium chloride hexahydrate.

Carboxylic acid esters are used broadly as solvents and as raw material for flavorings, resins, coating materials, adhesives and the like. A known method for producing carboxylic acid esters is to react a carboxylic acid anhydride with alcohol. Patent Literature 1 describes a method for producing phenyl (meth)acrylate by reacting a (meth)acrylic acid anhydride with phenol in the presence of alkali metal acetate.

PRIOR ART LITERATURE

Non-Patent Literature

Non-Patent Literature 1: Synthesis 2007, 3489-3496

Patent Literature

Patent Literature 1: JP2000-191590A

SUMMARY OF THE INVENTION

Problems to be Solved by the Invention

However, since the method for producing carboxylic acid anhydrides described in Non-Patent Literature 1 uses a greater amount of solvent, it is neither cost effective nor efficient. The inventors of the present invention have found that unless a solvent is added, reactions of di-t-butyl dicarbonate and carboxylic acid in the presence of magnesium chloride hexahydrate did not progress, or even if reactions progressed, the yield of produced carboxylic acid anhydride was low. In addition, when a (meth)acrylic acid anhydride was synthesized by a known production method, hardly any reaction was observed. Thus, substrate generality is found to be narrow.

In the method for producing carboxylic acid esters described in Patent Literature 1, it is hard to handle materials since alkali metal acetates are hygroscopic to a significantly high degree. In addition, regarding reactions of (meth)acrylic acid anhydride and alcohol, only the reactions carried out using phenol as alcohol are studied, and no detailed description is provided for other reactions in which phenols having a substituent are used as alcohol. In addition, the reaction temperature in the examples is high at 80° C. Such a method is neither cost effective nor efficient. Moreover, the obtained products are colored under the influence of byproducts. The inventors of the present invention have studied and found that when (meth)acrylic acid anhydride is synthesized by a known method, the reaction solution is colored and contains a small percentage of a compound having acetic acid or (meth)acrylic acid added to the double bond of the (meth)acrylic acid anhydride. Reactions of alcohol and (meth)acrylic acid anhydride containing such an adduct result in a byproduct ester derived from the adduct, and the yield and purity of a desired (meth)acrylic acid ester are thereby lowered. Moreover, using a known purification method, it is difficult to extract the (meth)acrylic acid ester from a mixture of the (meth)acrylic acid ester and the ester derived from the adduct.

Accordingly, the objective of the present invention is to provide a production method, which uses various types of carboxylic acids for producing corresponding carboxylic acid anhydrides and carboxylic acid esters under conditions near room temperature without using a solvent.

The inventors of the present invention have conducted intensive studies in consideration of the problems observed in conventional technology and have found that reactions using a specific catalyst achieve the above objective, and have completed the present invention.

A first aspect of the present invention is a method for producing a carboxylic acid anhydride represented by formula (II) below by reacting a carboxylic acid with a compound represented by formula (I) below in the presence of a Group 2 metal compound having an ionic ligand containing an oxygen atom. In formula (I), $R^1$ represents a $C_1$–$C_{20}$ hydrocarbon group. In formula (II), $R^2$ represents a $C_1$–$C_{20}$ hydrocarbon group.

[chemical formula 1]

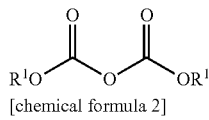

(I)

[chemical formula 2]

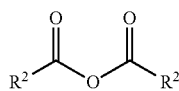

(II)

A second aspect of the present invention is a method for producing a carboxylic acid ester by producing a carboxylic acid anhydride using the above production method and by reacting the carboxylic acid anhydride with alcohol.

A third aspect of the present invention is a method for producing a carboxylic acid ester by reacting a compound represented by formula (I) below, a carboxylic acid and an alcohol in the presence of a Group 2 metal compound having an ionic ligand containing an oxygen atom. In formula (I), $R^1$ represents a $C_1$–$C_{20}$ hydrocarbon group.

[chemical formula 3]

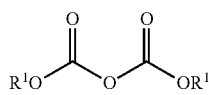

(I)

Effects of the Invention

The methods for producing carboxylic acid anhydrides according to the present invention are carried out without using a solvent. As a result, carboxylic acid anhydrides are obtained in more efficient and cost effective ways compared with conventional methods.

When the method for producing a carboxylic acid anhydride and the method for producing a carboxylic acid ester related to the present invention are employed, carboxylic acid anhydrides and carboxylic acid esters are obtained at high yield even under conditions near room temperature. Various types of carboxylic acid can be used as raw material in the method for producing a carboxylic acid anhydride related to the present invention. The substrate generality is remarkably broader than that in conventional methods. The method for producing a carboxylic acid ester is carried out by using various types of carboxylic acid and various types of alcohol as raw materials, and the substrate generality is remarkably broader than that in conventional methods.

MODE TO CARRY OUT THE INVENTION

In the present application, acrylic acid and methacrylic acid are collectively referred to as (meth)acrylic acid; acrylic acid anhydride and methacrylic acid anhydride are collectively referred to as (meth)acrylic acid anhydride; and acrylic acid esters and methacrylic acid esters are collectively referred to as (meth)acrylic acid esters. Also, an aryl group, arylalkyl group, arylalkenyl group, and arylalkynyl group are referred to as aryl groups. In the following description, a first method for producing a carboxylic acid anhydride may be referred to as "aspect 1" of the present invention, while second and third methods, each for producing a carboxylic acid ester, are respectively referred to as "aspect 2" and "aspect 3" of the present invention. "Aspect 1," "aspect 2" and "aspect 3" may also be collectively referred to as the "present invention."

In the following, "aspect 1" and "aspect 2" are described, and then "aspect 3" is described.

[Compound Represented by Formula (I)]

In a carboxylic acid anhydride production method of aspect 1 and a carboxylic acid ester production method of aspect 2, a compound represented by formula (I) is used as raw material. During the reaction, a compound represented by formula (I) may generate an intermediate product containing a component derived from the compound. However, a carboxylic acid anhydride and carboxylic acid ester obtained accordingly as the final product do not include a component derived from the compound.

[chemical formula 4]

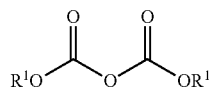

(I)

In formula (I), $R^1$ represents a $C_1$–$C_{20}$ hydrocarbon group. As long as $R^1$ represents a hydrocarbon group, the type and structure are not specifically limited. Hydrocarbon groups may be linear or branched, and may include a ring structure. In addition, an unsaturated bond or ether bond may be contained in the group.

Examples of a hydrocarbon group are an alkyl group, alkenyl group, alkynyl group and aryl group. Considering the ease of obtaining the compounds represented by formula (I), the number of carbon atoms in such a hydrocarbon group is 1~20, preferably 2~10, more preferably 3~7. More specifically, examples of a hydrocarbon group are an allyl group, t-butyl group, t-amyl group, benzyl group and the like. Also, specific examples of a compound represented by formula (I) are diallyl dicarbonate, di-t-butyl dicarbonate, di-t-amyl dicarbonate, dibenzyl dicarbonate and the like. Among them, a preferred example is di-t-butyl dicarbonate where $R^1$ is a t-butyl group, because a carboxylic acid anhydride represented by formula (II) is efficiently synthesized.

Commercially available compounds, or compounds synthesized by a known method and the like, may also be used as compounds represented by formula (I). Compounds represented by formula (I) may be used alone or in combination thereof.

[Carboxylic Acid]

In aspects 1 and 2, the type and structure of carboxylic acid used as raw material for producing a carboxylic acid anhydride and carboxylic acid ester are not specifically limited. For example, carboxylic acid is represented by "$R^2$—COOH," where $R^2$ represents a $C_1$–$C_{20}$ hydrocarbon group that may have a substituent. Such a hydrocarbon group may be linear or branched, and may include a ring structure. Also, an unsaturated bond or ether bond may be included in the group. "May have a substituent" means one or more of any substituent may be contained; for example, one or more of the following bonds, groups, atoms and the like may be contained: ester bond, amide bond, ether bond, sulfide bond, disulfide bond, urethane bond, nitro group, cyano group, ketone group, formyl group, acetal group, thioacetal group, sulfonyl group, halogen, silicon, phosphorus and the like.

Examples of a hydrocarbon group contained in carboxylic acid are an alkyl group, alkenyl group, alkynyl group, and aryl group. Considering the case of obtaining carboxylic acid, the number of carbon atoms in such a hydrocarbon group is preferred to be 1~20, more preferably 2~10. More specific examples of a hydrocarbon group are a vinyl group, isopropenyl group, t-butyl group, hexyl group, cyclohexyl group, phenyl group and the like.

Specific types of carboxylic acid are, for example, (meth)acrylic acid, pivalic acid, heptanoic acid, cyclohexanecarboxylic acid, benzoic acid and the like. Among them, $R^2$ is more preferred to be a vinyl group or isopropenyl group. Commercially available carboxylic acids, or those produced by a conventional method or the like, may also be used. (Meth)acrylic acid is especially preferred as a carboxylic acid.

The amount of carboxylic acid to be used in aspect 1 and aspect 2 is preferred to be 0.5~10 mol, more preferably 1~5 mol, relative to 1 mol of a compound represented by formula (I). Relative to 1 mol of the compound represented by formula (I), by setting the amount of carboxylic acid to be at least 0.5 mol, the yield of a carboxylic acid anhydride represented by formula (II) is enhanced, and by setting the amount of carboxylic acid to be no greater than 10 mol, the load on the post-reaction treatment process is reduced, thus improving cost effectiveness.

[Catalyst for Producing Carboxylic Acid Anhydride]

Regarding the method for producing a carboxylic acid anhydride in aspect 1 and aspect 2, the catalyst is a Group 2 metal compound having an ionic ligand containing an oxygen atom. Group 2 metal compounds are preferred to be neutral to basic, more preferably basic. Metals of Group 2 metal compounds are not specifically limited, but magnesium and calcium are preferred, more preferably magnesium. Since the solubility of a catalyst depends on the ionic ligand contained in the catalyst, the catalyst may be used as a homogeneous catalyst or heterogeneous catalyst.

Examples of a magnesium compound, which is a Group 2 metal compound of magnesium, are salts with inorganic acids such as oxide, hydroxide, carbonate, hydrogen carbonate, silicate, sulfate, ammonium sulfate, nitrate, phosphate, hydrogen phosphate, ammonium phosphate, and borate; salts with organic acids such as carboxylate and sulfonate; and complex salts such as acetylacetonate, hexafluoroacetylacetonate, porphyrin, phthalocyanine, cyclopentadiene and the like. These magnesium salts may be a hydrate or anhydride. Among them, oxide, hydroxide, carbonate, silicate, nitrate, phosphate, carboxylic acid ester, and complex salts are preferred.

More specific examples of a magnesium compound are magnesium oxide, magnesium hydroxide, magnesium carbonate, magnesium carbonate hydroxide (also known as magnesium basic carbonate), magnesium silicate, magnesium nitrate, magnesium phosphate, magnesium acetate, magnesium benzoate, magnesium (meth)acrylate, and magnesium acetylacetonate. Commercially available magnesium compounds, or those produced by a known method or the like, may also be used. Those listed above may be used alone or in combination thereof.

The amount of a catalyst to be used is not specifically limited, as long as it is capable of producing a carboxylic acid anhydride represented by formula (II). The amount is preferred to be 0.01~500 mol %, more preferably 0.1~50 mol %, relative to 1 mol of the compound represented by formula (I). By setting the amount of catalyst to be at least 0.01 mol % relative to 1 mol of a compound represented by formula (I), the yield of a carboxylic acid anhydride represented by formula (II) is enhanced. The amount of catalyst is set to be no greater than 500 mol % relative to 1 mol of a compound represented by formula (I), because an amount exceeding 500 mol % does not bring any significant enhancement to the effects of the catalyst.

In aspects 1 and 2, carboxylic acid and a compound represented by formula (I) are reacted in the presence of a catalyst. Here, regarding "in the presence of a catalyst," it is sufficient if the catalyst is present for at least part of the entire reaction process; it is not necessary for the catalyst to be always present in the entire reaction process. In the embodiments of the present invention, an addition of a catalyst to the reaction system meets the condition "in the presence of a catalyst." For example, after a catalyst is added to a reaction system, even if any change occurs to the catalyst during the reaction process, the condition "in the presence of a catalyst" is satisfied.

[Reaction Conditions for Producing Carboxylic Acid Anhydride]

Reaction conditions for producing a carboxylic acid anhydride in aspects 1 and 2 are not specifically limited, and may be modified appropriately during the reaction process. The type of reaction vessel is not specifically limited.

The reaction temperature is not specifically limited either, and may be set at 0~150° C., preferably 15~50° C. By setting the reaction temperature to be at least 0° C., reactions will progress efficiently. By setting the reaction temperature to be no higher than 150° C., the amount of byproducts is reduced and coloring of the reaction solution is suppressed.

The reaction time is not specifically limited, and it may be set for 0.5~48 hours, preferably 2~24 hours. By setting the reaction time to be at least 0.5 hours, the reaction will progress sufficiently. By setting the reaction time no longer than 48 hours, the amount of byproducts is reduced and coloring of the reaction solution is suppressed.

Neither ambient atmosphere nor pressure during reactions is specifically limited.

In the methods according to aspects 1 and 2, carboxylic acid anhydrides are produced without using a solvent. However, if the viscosity of a reaction solution is high or the like, a solvent may be used when applicable. The type of solvent is not specifically limited, and may be selected appropriately based on the reaction conditions. In such a case, one type of solvent may be used, or a combination of two or more solvents may also be used. The amount of solvent is not specifically limited, and may be determined appropriately.

It is not necessary to employ a specific method for feeding reaction materials (a compound represented by formula (I), carboxylic acid, catalyst, solvent, and the like). The materials may be introduced to the vessel all at once. Alternatively, part of or all the materials may be introduced by batch, continuously, or in combination thereof.

(Carboxylic Acid Anhydride)

The products obtained by the methods for producing carboxylic acid anhydrides according to aspects 1 and 2 are carboxylic acid anhydrides represented by formula (II) below. In the formula, $R^2$ is such a group as that described above when carboxylic acid is described.

[chemical formula 5]

(II)

When carboxylic acid used in the methods for producing carboxylic acid anhydrides according to aspects 1 and 2 is (meth)acrylic acid, (meth)acrylic acid anhydride is produced. Since (meth)acrylic acid anhydride is a compound that tends to polymerize, it is an option to add in advance a polymerization inhibitor so as to block polymerization. The timing of adding a polymerization inhibitor is not specifically limited. Adding at the time of initiating reaction is preferred because that makes it easier to handle the process.

A polymerization inhibitor to be used is not limited to any specific type, and any known polymerization inhibitor may be used; for example, hydroquinone monomethyl ether, hydroquinone, 4-hydroxy-2,2,6,6-tetramethylpiperidine 1-oxyl free radicals, 4,4'-butylidene bis(6-t-butyl-3-methylphenol), 6-t-butyl-2,4-xylenol, and the like. Those may be used alone or in combination thereof.

The amount of a polymerization inhibitor is preferred to be 0.001~0.5 parts by mass, more preferably 0.01~0.1 parts by mass, relative to 100 parts by mass of (meth)acrylic acid anhydride. In addition, a gas containing oxygen such as air may be introduced into the reaction system. The amount of such a gas may be determined appropriately according to reaction conditions and the like.

Regarding the methods for producing carboxylic acid anhydrides in aspects 1 and 2, a carboxylic acid anhydride represented by formula (II) may be used as is or purified for use in the following reaction. Purification conditions are not specifically limited and may be modified appropriately during the reaction process or at the time the reaction is completed. For example, after the reaction is finished, a carboxylic acid anhydride may be purified from the obtained reaction mixture by using a method such as vacuum distillation and chromatography. Those methods may be used alone or in combination thereof.

[Alcohol]

In aspect 2, alcohol is used for producing a carboxylic acid ester. The alcohol to be used is not limited to any specific type or structure. For example, alcohol is described as "$R^3$—OH"; $R^3$ is preferred to be a $C_1$~$C_{30}$ hydrocarbon group that may contain a substituent. Such a hydrocarbon group may be linear or branched, and may include a ring structure and an unsaturated bond. "May have a substituent" means one or more of any substituent may be contained; for example, one or more of the following bonds, groups, atoms and the like may be contained: ester bond, amide bond, ether bond, sulfide bond, disulfide bond, urethane bond, nitro group, cyano group, ketone group, formyl group, acetal group, thioacetal group, sulfonyl group, halogen, silicon, phosphorus and the like.

A hydrocarbon group contained in alcohol may be an alkyl group, alkenyl group, alkynyl group or aryl group, for example. Considering the ease of obtaining alcohol, the number of carbon atoms in a hydrocarbon group is preferred to be 1~30, more preferably 2~20. Among them, an aryl group is more preferred. The type of alcohol is preferred to be aromatic, in particular, phenol, phenylphenol, naphthol, and the like.

Commercially available alcohols, or those produced by a known method or the like, may also be used. One type or multiple types of alcohol may be used, and polyvalent alcohols may be used as well.

The method for introducing alcohol into a reaction vessel is not specifically limited; the entire amount may be introduced all at once, by batch, or continuously. Alternatively, such methods may be combined. Alcohol may be added at any time during the reaction process; alcohol may be added either during or after the production process of a carboxylic acid anhydride. Alternatively, alcohol may be added to a carboxylic acid anhydride after it is produced, isolated and purified.

The amount of alcohol to be used is preferred to be 0.1~10 mol, more preferably 0.5~5 mol, relative to 1 mol of a compound represented by formula (I) or a compound represented by formula (II). Regarding the amount of alcohol relative to 1 mol of a compound represented by formula (I) or a compound represented by formula (II), when the amount is set to be at least 0.1 mol, the yield of the carboxylic acid ester is enhanced, and when the amount is set to be no greater than 10 mol, the load on the post-reaction treatment process is reduced, thus improving cost effectiveness.

[Catalyst for Producing Carboxylic Acid Ester]

The catalyst used for the later reaction step in aspect 2 is preferred to be an organic acid, organic base, inorganic acid, inorganic base or the like which is usually used in esterification reactions. Among them, the aforementioned catalysts used for producing carboxylic acid anhydrides in aspects 1 and 2 are also effective in synthesizing carboxylic acid esters, and steps from the production of a carboxylic acid anhydride through the production of a carboxylic acid ester may be performed in the same vessel. In addition, those catalysts are preferred since it is easier to separate them from the obtained carboxylic acid ester. Those catalysts may be used in either homogeneous or heterogeneous catalytic reactions. They may be used alone or in combination thereof. The amount of catalyst is not specifically limited, as long as it is capable of producing carboxylic acid esters.

[Reaction Conditions for Producing Carboxylic Acid Ester]

Reaction conditions in the method for producing carboxylic acid esters according to aspect 2 are not specifically limited, and may be modified appropriately during the reaction process.

A reaction vessel to be used is not limited to any specific type, and the method for introducing reaction materials into a vessel is not specifically limited. The reaction temperature is not set at any particular temperature, and it may be 0~150° C., preferably 15~50° C. By setting the reaction temperature at 0° C. or higher, reactions will progress efficiently, and by setting the reaction temperature at no higher than 150° C., the amount of byproducts is reduced and the coloring of the reaction solution is suppressed.

The reaction time is not specifically limited either, and it may be set for 0.5~48 hours, preferably 2~24 hours, after alcohol is added. By setting the reaction time to be at least 0.5 hours, the reaction will progress sufficiently. By setting the reaction time to be no longer than 48 hours, the amount of byproducts is reduced and coloring of the reaction solution is suppressed.

Neither ambient atmosphere nor pressure during reactions is specifically limited.

The reaction in aspect 2 may be carried out without using any solvent. However, if the viscosity of a reaction solution is high or the like, a solvent may be used when applicable. The type of solvent is not specifically limited, and may be selected appropriately based on reaction conditions. In such a case, one type of solvent may be used, or a combination of two or more solvents may also be used. The amount of solvent is not specifically limited, and may be determined appropriately.

[Carboxylic Acid Ester]

The product obtained by the production method of aspect 2 is represented as "$R^2COOR^3$". $R^2$ and $R^3$ were described when carboxylic acids and alcohol were described above.

When a (meth)acrylic acid ester is produced by the production method of aspect 2, since a (meth)acrylic acid ester to be produced is a compound that tends to polymerize, it is an option to add a polymerization inhibitor so as to prevent polymerization. A polymerization inhibitor to be used is not limited to any specific type, and any known polymerization inhibitors may be used alone or in combination thereof. The amount of a polymerization inhibitor is preferred to be 0.001~0.5 parts by mass, more preferably 0.01~0.1 parts by mass, relative to 100 parts by mass of a (meth)acrylic acid ester. In addition, an oxygen-containing gas such as air may be introduced into the reaction system. The amount of such a gas may be determined appropriately according to reaction conditions and the like.

In aspect 2, the obtained carboxylic acid ester may be used as is or purified for use in the following reaction. Purification conditions are not specifically limited and may be modified appropriately during the reaction process or at the time the reaction is completed. For example, after the reaction is finished, a carboxylic acid ester may be purified from the obtained reaction mixture by using a method such as vacuum distillation or chromatography. The method may be used alone or in combination thereof.

[Aspect 3]

Aspect 3 is a method for producing a carboxylic acid ester by reacting carboxylic acid, alcohol and a compound represented by formula (I) in the presence of a Group 2 metal compound having an ionic ligand containing an oxygen atom. In aspect 3, alcohol is added in the reaction system prior to initiating the reaction.

The catalyst used in aspect 3 is a Group 2 metal compound, which is the same type as the catalyst used in aspects 1 and 2. In aspect 3, the definition of "in the presence of a catalyst" is the same as that in aspects 1 and 2.

The carboxylic acid used as raw material in aspect 3 is the same type of compound as the carboxylic acid used in aspects 1 and 2, and is selected based on the same criteria as those applied to aspects 1 and 2.

The amount of carboxylic acid to be used in aspect 3 is preferred to be 0.5~2 mol, more preferably 0.7~1.5 mol, relative to 1 mol of a compound represented by formula (I). By setting the amount of carboxylic acid to be at least 0.5 mol relative to 1 mol of the compound represented by formula (I), the yield of carboxylic acid ester is enhanced. By setting the amount of carboxylic acid to be no greater than 2 mol relative to 1 mol of the compound represented by formula (I), the load on the post-reaction treatment process is reduced, thus improving cost effectiveness.

The alcohol used as raw material in aspect 3 is the same type of compound as the alcohol used in aspects 1 and 2, and the type and the amount to be used are selected based on the same criteria as those in aspects 1 and 2.

Reaction conditions in the method for producing a carboxylic acid ester according to aspect 3 are not specifically limited, and may be modified appropriately during the reaction process.

A reaction vessel to be used is not limited to any specific type, and the method for introducing reaction materials into a vessel is not specifically limited. The reaction temperature is not set at any particular temperature, and it may be 0~150° C., preferably 15~50° C. By setting the reaction temperature at 0° C. or higher, reactions will progress efficiently, and by setting the reaction temperature at no higher than 150° C., the amount of byproducts is reduced and the coloring of the reaction solution is suppressed.

The reaction time is not specifically limited either, and it may be set for 0.5~48 hours, preferably 2~24 hours, after alcohol is added. By setting the reaction time to be at least 0.5 hours, the reaction will progress sufficiently. By setting the reaction time to be no longer than 48 hours, the amount of byproducts is reduced and coloring of the reaction solution is suppressed.

Neither ambient atmosphere nor pressure during reactions is specifically limited.

The reaction in aspect 3 may be carried out without using any solvent. However, if the viscosity of a reaction solution is high or the like, a solvent may be used when applicable. The type of solvent is not specifically limited, and may be selected appropriately based on reaction conditions. In such a case, one type of solvent may be used, or a combination of two or more solvents may also be used. The amount of solvent is not specifically limited, and may be determined appropriately.

The storage conditions, purification process and the like of the obtained (meth)acrylic acid esters are the same as those applied in aspect 2.

EXAMPLES

In the following, the present invention is described in detail with reference to examples. However, the present invention is not limited to those examples, and any modifications may be entered within a scope that does not deviate from the gist of the present invention. Examples 1~21 and Comparative Examples 1~7 each relate to production of a carboxylic acid anhydride, whereas Examples 22~30 each relate to production of a carboxylic acid ester.

Di-t-butyl dicarbonate used in the following Examples and Comparative Examples is a compound at a purity of 98 mass %, made by Tokyo Chemical Industry Co., Ltd. In formula (I), $R^1$ is $C(CH_3)_3$. In addition, tetrahydrofuran (hereinafter abbreviated as "THF") is a special grade (water content of 0.05% or less) or dehydration grade (water content of 0.001% or less), made by Kanto Chemical Co., Inc. The yield of each product was measured as follows.

[1. Yield of Carboxylic Acid Anhydride]

After the completion of reactions, a standard substance (anisole or 1,1,2,2-tetrachloroethane) was added to the obtained reaction mixture. The mixture was dissolved in deuterated chloroform ($CDCl_3$) and $^1$H-NMR (270 MHz) analysis was conducted. By converting the integrated intensity of a signal in a spectrum, the amount (mmol) of the produced carboxylic acid anhydride was determined. Then, the yield of the carboxylic acid anhydride was calculated by the following formula (1).

$$\text{Yield of carboxylic acid anhydride (\%)} = (P_1/R_1) \times 100 \quad (1)$$

$P_1$: the amount of produced carboxylic acid anhydride (mmol)
$R_1$: the amount of di-t-butyl dicarbonate used in reaction (mmol)

[2. Yield of Carboxylic Acid Ester]

Using the same procedure employed to measure the yield of a produced carboxylic acid anhydride, the amount of produced carboxylic acid ester (mmol) was obtained. Then, the yield of carboxylic acid ester was calculated by the following formula (2).

$$\text{Yield of carboxylic acid ester (\%)} = (P_2/R_2) \times 100 \quad (2)$$

$P_2$: the amount of produced carboxylic acid ester (mmol)
$R_2$: the amount of alcohol used in reaction (mmol)

Example 1

In a 50 mL-volume eggplant-shaped flask, 0.520 grams (6 0 mmol) of methacrylic acid, 0.673 grams (3.0 mmol) of di-t-butyl dicarbonate, and 0.066 grams (0.1 mmol, 4 mol % relative to di-t-butyl dicarbonate) of magnesium carbonate hydroxide were added successively. Reactions were carried out at 25° C. while the mixture was being stirred. Accordingly, methacrylic acid anhydride was produced. The reaction results obtained 4 hours after the start of reactions are shown in Table 1.

Examples 2~13

In each example, methacrylic acid anhydride was produced under conditions the same as in Example 1 except that magnesium carbonate hydroxide as a catalyst was replaced with the type and amount (4 mol % relative to di-t-butyl dicarbonate) of the metal compound shown in Table 1. The reaction results obtained 4 hours after the start of reactions are shown in Table 1.

Examples 14~20

In each example, methacrylic acid anhydride was produced under conditions the same as in Example 1 except that methacrylic acid was replaced with the type of carboxylic acid (6.0 mmol) shown in Table 1, and the amount of magnesium carbonate hydroxide relative to di-t-butyl dicarbonate was changed to 4 mol % or 8 mol %, while the rest of the conditions were set to be the same as in Example 1. The reaction results obtained 4~12 hours after the start of reactions are shown in Table 1.

Example 21

In a 50 mL-volume eggplant-shaped flask, 5.000 grams (40.9 mmol) of benzoic acid, 4.559 grams (20 5 mmol) of di-t-butyl dicarbonate, 20 mL of THF (special grade) and 0.891 grams (1.6 mmol, 8 mol % relative to di-t-butyl dicarbonate) of magnesium carbonate hydroxide were added successively. Reactions were carried out at 25° C. while the mixture was being stirred. Accordingly, benzoic acid anhydride was produced. The reaction results obtained 24 hours after the start of reactions are shown in Table 1.

Comparative Examples 1 and 2

In each comparative example, production of methacrylic acid anhydride was tried under conditions the same as in Example 1 except that magnesium carbonate hydroxide was replaced with magnesium chloride hexahydrate (4 mol % or 20 mol % relative to di-t-butyl dicarbonate). The reaction results obtained 4 hours after the start of reactions are shown in Table 1.

Comparative Example 3

Heptanoic acid anhydride was produced under conditions the same as in Example 1 except that magnesium carbonate hydroxide was replaced with magnesium chloride hexahydrate (20 mol % relative to di-t-butyl dicarbonate), and methacrylic acid was replaced with heptanoic acid (6.0 mmol). The reaction results obtained 6 hours after the start of reactions are shown in Table 1.

Comparative Examples 4 and 5

In each comparative example, methacrylic acid anhydride was produced under conditions the same as in Example 1 except that magnesium carbonate hydroxide was replaced with magnesium chloride hexahydrate (20 mol % relative to di-t-butyl dicarbonate), and 6 mL of THF (dehydration grade) was used. The reaction results obtained 4 hours or 24 hours after the start of reactions are shown in Table 1.

Comparative Examples 6 and 7

In each comparative example, methacrylic acid anhydride was produced under conditions the same as in Example 1 except that magnesium carbonate hydroxide was replaced with magnesium chloride hexahydrate (20 mol % relative to di-t-butyl dicarbonate), and 6 mL of THF (special grade) was used. The reaction results obtained 4 hours or 24 hours after the start of reactions are shown in Table 1.

Example 22

In a 50 mL-volume eggplant-shaped flask, 0.700 grams (9.7 mmol) of acrylic acid, and 1.082 grams (4.9 mmol) of di-t-butyl dicarbonate, 0.106 grams (0.2 mmol, 4 mol % relative to di-t-butyl dicarbonate) of magnesium carbonate hydroxide were added successively. Reactions were carried out for 4 hours at 25° C. while the mixture was being stirred.

In the mixture obtained above, 0.457 grams (4.9 mmol) of phenol was added, and reactions were carried out at 25° C. while the mixture was being stirred. Accordingly, phenyl acrylate was produced. The reaction results obtained 6 hours after the addition of phenol are shown in Table 2. The yield of acrylic acid anhydride prior to adding phenol was 90%.

Examples 23 and 24

In each example, acrylic acid ester was produced under conditions the same as in Example 22 except that phenol was replaced with the type of alcohol (4.9 mmol) shown in Table 2. The reaction results obtained 6 hours after adding alcohol are shown in Table 2.

Example 25

Phenyl methacrylate was produced under conditions the same as in Example 22 except that acrylic acid was replaced with methacrylic acid (9.7 mmol). The reaction results obtained 6 hours after the addition of phenol are shown in Table 2. The yield of methacrylic acid anhydride prior to adding phenol was 94%.

Examples 26 and 27

In each example, a methacrylic acid ester was produced under conditions the same as in Example 25 except that phenol was replaced with the type of alcohol (4.9 mmol) shown in Table 2. The reaction results obtained 6 hours after adding alcohol are shown in Table 2.

Example 28

This is an example for producing a carboxylic acid ester by adding alcohol during the production of a carboxylic acid anhydride. In a 50 mL-volume eggplant-shaped flask, 0.520 grams (6.0 mmol) of methacrylic acid, 1.345 grams (6.0 mmol) of di-t-butyl dicarbonate, and 0.027 grams (0 1 mmol, 2 mol % relative to di-t-butyl dicarbonate) of magnesium acetylacetonate were added successively. Reactions were carried out for 4 hours at 25° C. while the mixture was being stirred.

In the mixture obtained above, 0.568 grams (6.0 mmol) of phenol was added, and reactions were carried out at 25° C. while the mixture was being stirred. Accordingly, phenyl methacrylate was produced. The reaction results obtained 24 hours after the addition of phenol are shown in Table 2. The yield of methacrylic acid anhydride prior to adding phenol was 40%.

Example 29

This is an example of aspect 3, namely, an example for producing a carboxylic acid ester by adding alcohol before the production of a carboxylic acid anhydride. In a 50 mL-volume eggplant-shaped flask, 1.200 grams (13.9 mmol) of methacrylic acid, 3.104 grams (13.9 mmol) of di-t-butyl dicarbonate, 1.312 grams (13.9 mmol) of phenol, and 0.031 grams (0.1 mmol, 1 mol % relative to di-t-butyl dicarbonate) of magnesium acetylacetonate were added successively. Reactions were carried out at 25° C. while the mixture was being stirred. Accordingly, phenyl methacrylate was produced. The reaction results obtained 5 hours after the start of reactions are shown in Table 2.

Example 30

In a 50 mL-volume eggplant-shaped flask, 1.500 grams (11.5 mmol) of heptanoic acid, 1.283 grams (5.8 mmol) of di-t-butyl dicarbonate, 0.125 grams (0.2 mmol, 4 mol % relative to di-t-butyl dicarbonate) of magnesium carbonate hydroxide were added successively. Reactions were carried out for 12 hours at 25° C. while the mixture was being stirred. The mixture containing heptanoic acid anhydride was diluted with ethyl acetate and washed with pure water. The washed mixture was separated into an organic phase and water phase, and 1.257 grams (5.2 mmol, 90% yield) of heptanoic acid anhydride was obtained by concentrating the organic phase. Into the heptanoic acid anhydride, 0.488 grams (5.2 mmol) of phenol, and 0.015 grams (0.3 mmol, 5 mol % relative to phenol) of magnesium hydroxide were added successively, which was then subjected to reactions at 25° C. while the mixture was being stirred. Accordingly, phenyl heptanoate was produced. The reaction results obtained 17 hours after the start of reactions are shown in Table 2.

TABLE 1

|  | Carboxylic Acid | Catalyst | Amount of Catalyst (mol %) | Solvent | Reaction Time (h) | Yield of Carboxylic Acid Anhydride (%) |
|---|---|---|---|---|---|---|
| Example 1 | methacrylic acid | magnesium carbonate hydroxide | 4 | — | 4 | 94 |
| Example 2 | methacrylic acid | magnesium hydroxide | 4 | — | 4 | 85 |
| Example 3 | methacrylic acid | magnesium oxide | 4 | — | 4 | 88 |
| Example 4 | methacrylic acid | magnesium acetylacetonate | 4 | — | 4 | 74 |
| Example 5 | methacrylic acid | magnesium acetate tetrahydrate | 4 | — | 4 | 86 |
| Example 6 | methacrylic acid | magnesium benzoate trihydrate | 4 | — | 4 | 86 |
| Example 7 | methacrylic acid | magnesium methacrylate | 4 | — | 4 | 99 |
| Example 8 | methacrylic acid | magnesium silicate | 4 | — | 4 | 56 |
| Example 9 | methacrylic acid | magnesium phosphate octahydrate | 4 | — | 4 | 49 |
| Example 10 | methacrylic acid | magnesium nitrate hexahydrate | 4 | — | 4 | 20 |
| Example 11 | methacrylic acid | calcium oxide | 4 | — | 4 | 12 |
| Example 12 | methacrylic acid | calcium hydroxide | 4 | — | 4 | 15 |
| Example 13 | methacrylic acid | calcium acetylacetonate | 4 | — | 4 | 16 |
| Example 14 | heptanoic acid | magnesium carbonate hydroxide | 4 | — | 6 | 67 |
| Example 15 | heptanoic acid | magnesium carbonate hydroxide | 4 | — | 12 | 94 |
| Example 16 | acrylic acid | magnesium carbonate hydroxide | 4 | — | 4 | 90 |
| Example 17 | cyclohexane carboxylic acid | magnesium carbonate hydroxide | 8 | — | 6 | 98 |
| Example 18 | pivalic acid | magnesium carbonate hydroxide | 8 | — | 6 | 97 |
| Example 19 | monomethyl adipate | magnesium carbonate hydroxide | 8 | — | 6 | 95 |
| Example 20 | 4-chlorobutyric acid | magnesium carbonate hydroxide | 8 | — | 6 | 95 |
| Example 21 | benzoic acid | magnesium carbonate hydroxide | 8 | THF (special grade) | 24 | 98 |
| Comp. Example 1 | methacrylic acid | magnesium chloride hexahydrate | 4 | — | 4 | 0 |
| Comp. Example 2 | methacrylic acid | magnesium chloride hexahydrate | 20 | — | 4 | 0 |
| Comp. Example 3 | heptanoic acid | magnesium chloride hexahydrate | 20 | — | 6 | 8 |
| Comp. Example 4 | methacrylic acid | magnesium chloride hexahydrate | 20 | THF (dehydration grade) | 4 | 3 |
| Comp. Example 5 | methacrylic acid | magnesium chloride hexahydrate | 20 | THF (dehydration grade) | 24 | 22 |
| Comp. Example 6 | methacrylic acid | magnesium chloride hexahydrate | 20 | THF (special grade) | 4 | 14 |
| Comp. Example 7 | methacrylic acid | magnesium chloride hexahydrate | 20 | THF (special grade) | 24 | 67 |

TABLE 2

|  | Carboxylic Acid | Catalyst | Amount of Catalyst (mol %) | Alcohol | Reaction Time after Adding Alcohol (h) | Yield of Carboxylic Acid Ester (%) |
|---|---|---|---|---|---|---|
| Example 22 | acrylic acid | magnesium carbonate hydroxide | 4 | phenol | 6 | 53 |
| Example 23 | acrylic acid | magnesium carbonate hydroxide | 4 | 2-phenylphenol | 6 | 30 |
| Example 24 | acrylic acid | magnesium carbonate hydroxide | 4 | 1-naphthol | 6 | 53 |
| Example 25 | methacrylic acid | magnesium carbonate hydroxide | 4 | phenol | 6 | 65 |
| Example 26 | methacrylic acid | magnesium carbonate hydroxide | 4 | 2-phenylphenol | 6 | 49 |
| Example 27 | methacrylic acid | magnesium carbonate hydroxide | 4 | 1-naphthol | 6 | 64 |
| Example 28 | methacrylic acid | magnesium acetylacetonate | 2 | phenol | 24 | 90 |

TABLE 2-continued

| | Carboxylic Acid | Catalyst | Amount of Catalyst (mol %) | Alcohol | Reaction Time after Adding Alcohol (h) | Yield of Carboxylic Acid Ester (%) |
|---|---|---|---|---|---|---|
| Example 29 | methacrylic acid | magnesium acetylacetonate | 1 | phenol | 5 | 86 |
| Example 30 | heptanoic acid | magnesium hydroxide | 5 | phenol | 17 | 80 |

INDUSTRIAL APPLICABILITY

The methods related to the present invention are capable of producing carboxylic acid anhydrides and carboxylic acid esters in more efficient and cost effective ways than conventional methods. In addition, the methods related to the present invention are capable of producing carboxylic acid anhydrides and carboxylic acid esters at high yield under relaxed reaction conditions. Moreover, since various types of carboxylic acid and alcohol may be used as materials in the production methods related to the present invention, substrate generality is significantly broader than in conventional production methods.

The invention claimed is:

1. A method for producing a carboxylic acid anhydride of formula (II), the method comprising:
reacting a carboxylic acid comprising a group $R^2$ which is a $C_1$-$C_{20}$ hydrocarbon group that may have a substituent with a compound of formula (I) in the presence of a Group 2 metal compound comprising an ionic ligand containing an oxygen atom as a catalyst:

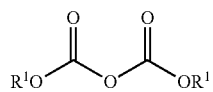
(I)

where the metal of the Group 2 metal compound is macnesium or calcium and $R^1$ is a $C_1$-$C_{20}$ hydrocarbon group,

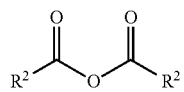
(II)

and where $R^2$ in formula (II) is the $R^2$ group of the carboxylic acid.

2. The method according to claim 1, wherein the Group 2 metal compound is one or more selected from the group consisting of an oxide salt, a hydroxide salt, a silicate salt, a nitrate salt, a phosphate salt, a carbonate salt, a carboxylate salt and a complex salt.

3. The method according to claim 1, wherein the metal of the Group 2 metal compound is magnesium.

4. The method according to claim 1 wherein the compound of the formula (I) is di-t-butyl Bicarbonate.

5. The method according to claim 1, wherein the carboxylic acid is (meth)acrylic acid.

6. A method for producing a carboxylic acid ester, the method comprising:
reacting the carboxylic acid anhydride obtained by the method according to claim 1 with an alcohol.

7. The method according to claim 6, wherein the alcohol is aromatic alcohol.

8. A method for producing a carboxylic acid ester, the method comprising:
reacting a compound of formula (I), a carboxylic acid and an alcohol in the presence of a Group 2 metal compound comprising an ionic ligand containing an oxygen atom as a catalyst:

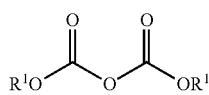
(I)

where $R^1$ is a $C_1$-$C_{20}$ hydrocarbon group and the metal of the Group 2 metal compound is magnesium or calcium.

9. The method according to claim 8, wherein the metal of the Group 2 metal compound is magnesium.

10. The method according to claim 8, wherein the compound of the formula (I) is di-t-butyl dicarbonate.

11. The method according to claim 8, wherein the carboxylic acid is (meth)acrylic acid.

12. The method according to claim 8, wherein the alcohol is an aromatic alcohol.

13. The method according to claim 1, wherein the method is conducted in the absence of solvent.

14. The method according to claim 1, wherein the Group 2 metal compound comprising an ionic ligand containing an oxygen atom is selected from magnesium oxide, hydroxide, carbonate, hydrogen carbonate, silicate, sulfate, ammonium sulfate, nitrate, phosphate, hydrogen phosphate, ammonium phosphate, and borate salts.

15. The method according to claim 1, wherein the Group 2 metal compound comprising an ionic ligand containing an oxygen atom is selected from magnesium carboxylate and sulfonate salts.

16. The method according to claim 1, wherein the Group 2 metal compound comprising an ionic ligand containing an oxygen atom is selected from magnesium acetylacetonate, hexafluoroacetylacetonate, porphyrin, phthalocyanine, and cyclopentadiene complex salts.

17. The method according to claim 1, wherein the Group 2 metal compound comprising an ionic ligand containing an oxygen atom is selected from magnesium oxide, hydroxide, carbonate, silicate, nitrate, phosphate, and carboxylic acid ester salts.

18. The method according to claim 1, wherein the Group 2 metal compound comprising an ionic ligand containing an oxygen atom is selected from magnesium oxide, magnesium hydroxide, magnesium carbonate, magnesium carbonate hydroxide, magnesium silicate, magnesium nitrate, magnesium phosphate, magnesium acetate, magnesium benzoate, magnesium (meth)acrylate, and magnesium acetylacetonate.

19. The method according to claim 1, wherein the Group 2 metal compound comprising an ionic ligand containing an oxygen atom is selected from magnesium carbonate hydroxide, magnesium hydroxide, magnesium oxide, magnesium acetyl acetonate, magnesium acetate tetrahydrate, magnesium benzoate trihydrate, magnesium methacrylate, magnesium silicate, magnesium phosphate octahydrate, magnesium nitrate hexahydrate, calcium oxide, calcium hydroxide, calcium acetylacetonate, and magnesium carbonate hydroxide.

\* \* \* \* \*